United States Patent [19]

Fruehwirth

[11] Patent Number: Plant 7,229

[45] Date of Patent: May 15, 1990

[54] POINSETTIA PLANT '130'

[75] Inventor: Franz Fruehwirth, Encinitas, Calif.

[73] Assignee: Paul Ecke Ranch, Inc., Encinitas, Calif.

[21] Appl. No.: 263,493

[22] Filed: Oct. 27, 1988

[51] Int. Cl.[5] ..... A01H 5/00
[52] U.S. Cl. ..... Plt./86
[58] Field of Search ..... Plt./86

[56] References Cited

U.S. PATENT DOCUMENTS 4,724,276 2/1988 Ecke, Jr. ..... 800/1

*Primary Examiner*—James R. Feyrer
*Attorney, Agent, or Firm*—Arnold, White & Durkee

[57] ABSTRACT

The present disclosure describes a new Poinsettia cultivar, '130', having bright yellow flower bracts and dark green foliage. The contrast between the yellow bracts and green foliage are particularly pleasing. The overall height of a flowering plant is relatively short, with short bract petioles resulting in a tight center to the flower bract presentation.

1 Drawing Sheet

BACKGROUND OF THE INVENTION

Poinsettia '130' is most easily identified by its bright yellow flower bracts. This is unique because Poinsettias with yellow flower bracts are not known in commerce. This cultivar also has very dark green foliage which make a pleasing contrast to the yellow flower bracts. The overall height of a flowering plant is relatively short. The bract petioles are short, resulting in tight center to the flower bract presentation.

This new Poinsettia cultivar originated as a seedling from cross pollination of poinsettias in a greenhouse in Encinitas, Calif. It was selected from many seedlings because of its bright yellow flower bracts which distinguishes it from other poinsettia cultivars, and seems to make it a desirable plant for commercial greenhouse production. After selection, vegetatively reproduction of this plant by stem cuttings for test purposes in Encinitas, Calif., and clones of the plant were subjected to successive generations of vegetative propagation which demonstrated that its yellow flower bracts and other distinctive characteristics hold true from generation to generation.

DESCRIPTION OF THE PHOTOGRAPHS

Poinsettia '130' is illustrated in the accompanying color photographs. The upper photo is a side view of a branched plant in full flower. The lower photo is a top view of a plant showing flower and bract formation.

DESCRIPTION OF THE PLANT

The following is a detailed description of this new Poinsettia as observed in a greenhouse in Encinitas, Calif., during December, 1987. Recorded observations from flowering plants, grown as 3 unpinched plants per pot were observed. The pot was 14 cm. in diameter and 11 cm. in height. Color designations were compared to the 1986 edition of R.H.S. Colour Chart, first published in 1966 by the Royal Horticultural Society, London, England.

THE PLANT

Origin: Seedling, which was further treated by the process set forth in U.S. Pat. No. 4,724,276, to impart self-branching characteristics thereto.

Classification:

*Botanic.*—*Euphorbia pulcherrima* Willd.

*Common name.*—Poinsettia.

*Cultivar name.*—'130'.

Form: Shrub.

Height: Short.

Growth habit: As a single stemmed plant, upright and short. The application of a chemical growth retardant may not be needed to restrict height for commercial pot plant reproduction. Observation of 3 plants in a pot with an overall height of 33 cm. and an overall width of 36 cm. were made. The bract diameter of individual flowers was 24 cm.

Branching: Branching can be enhanced by removal of the stem tip. Then, 4–5 flowering branches may develop on a single plant.

Growth rate: Very fast. Rooting of stem cuttings occurs in 12–18 days under intermittent mist. The plant will flower in about ten weeks under continuous long night conditions and night temperatures of about 16–18 degrees C.

Foliage: The foliage is clean and uniformly green from bottom to top of the plant. The leaves are of small size, leaf blades typically being about 9–11 cm. long and about 6–8 cm. wide with leaf petioles about 4–5 cm. long. The dark green leaves are moderately rugose, giving them an unusual and attractive appearance unlike most known cultivars of Poinsettia.

Leaf shape: Typical leaves are ovate with obtuse bases and acuminate tips. Leaf margins are usually entire with some modest lobing on each side of the blade.

Color:

*Upper side.*—Dark Green, much darker than R.H.S. 139A.

*Under side.*—Green, darker than R.H.S. 133A.

Retention: The foliage retention is of average duration under low light intensities in the consumer's home.

Bracts: Generally there are 21–24 uniformly colored bracts of various sizes subtending the cyathia. The primary bracts have blades typically 11 cm. long and 7–8 cm. wide with petioles about 2 cm long. The bright yellow bracts are moderately rugose, which enhances their attractive appearance.

Shape: Bracts are mostly ovate with acute bases and acuminate tips. Primary bracts are often lobed with two indentations on either side of the bract.

Color:

*Upper side.*—Bright yellow, darker than R.H.S. 8B; more bronze than R.H.S. 8A.

*Under side.*—Yellow, darker than R.H.S. 8B; more bronze than R.H.S. 8A.

Cyathia: Generally, 15–18 cyathia (flowers) are present when the plant is in "full bloom". Each cyathium is about 8 mm long and about 5–6 mm wide, green in color, and fringed with yellow at the distal end. Usually, one golden yellow nectar cup protrudes from the side of the cyathium. The flower pedicel is also green and about 3–4 mm in long. The anthers protruding from the cyathia are white.

What is claimed:

1. A new and distinct Poinsettia cultivar, substantially as herein shown and described, distinguished by its bright yellow flower bracts and dark green foliage.

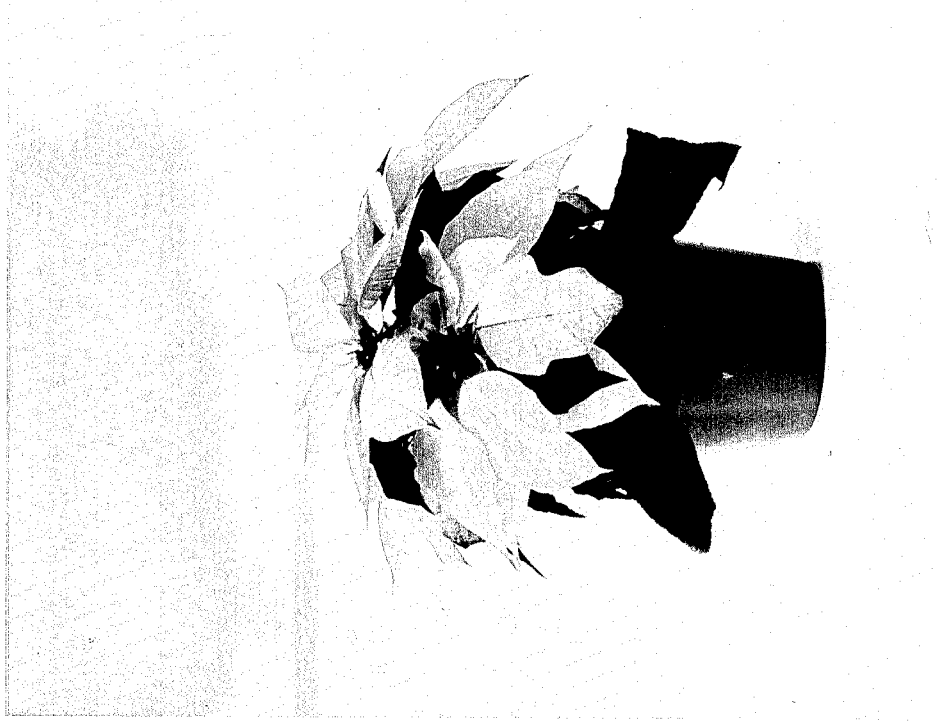
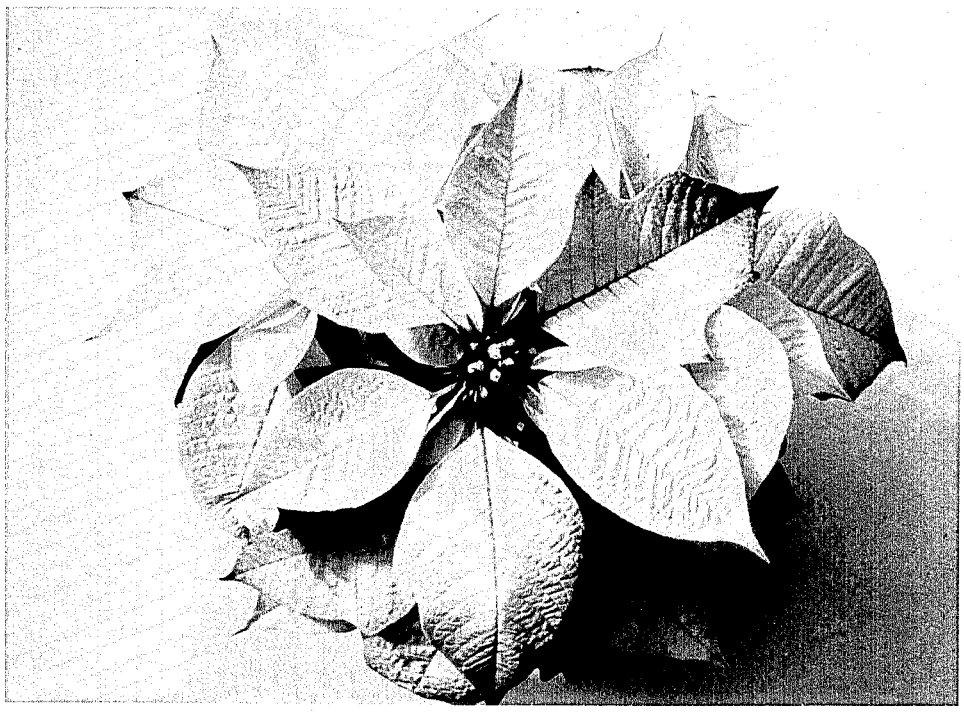

* * * * *